United States Patent [19]
Wong et al.

[11] Patent Number: 5,876,855
[45] Date of Patent: *Mar. 2, 1999

[54] PRESSURE-SENSITIVE ADHESIVE SUITABLE FOR SKIN AND METHOD OF PREPARING

[75] Inventors: Roy Wong, White Bear Lake, Minn.; Dennis L. Krueger, Hudson, Wis.; Patrick D. Hyde, Burnsville, Minn.; Felix P. Lau, Austin, Tex.; Eumi Pyun, Austin, Tex.; Pamela S. Tucker, Austin, Tex.

[73] Assignee: Minnesota Mining and Manufacturing Company, St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 577,923

[22] Filed: Dec. 22, 1995

[51] Int. Cl.$^6$ .............................. C09J 7/02; C09J 109/00; C09J 131/06

[52] U.S. Cl. .......................... 428/355 BL; 428/355 AC; 525/71; 525/80

[58] Field of Search .......................... 428/355, 355 AC, 428/355 BL; 525/71, 80

[56] References Cited

U.S. PATENT DOCUMENTS 4,248,748  2/1981  McGrath et al. .

FOREIGN PATENT DOCUMENTS 0 349 216     6/1989   European Pat. Off. .
0 437 068 A2 12/1990   European Pat. Off. .
WO 96/25469   8/1996   WIPO .

OTHER PUBLICATIONS

Journal of Adhesion, vol. 47, 1 Jan. 1994, pp. 165–177, XP000568496, Naruse S et al; "Miscibility and PSA Performance of Acrylic Copolymer and Tackifier Resin Systems*").

Journal of Applied Polymer Science, vol. 57, No. 2, 11 Jul. 1995, pp. 175–185, XP000541044, Kim H –J et al; "Miscibility Between Components of Acrylic Pressure–Sensitive Adhesives: Phase Diagrams of Poly(Butyl Acrylate- –Co–Acrylic Acid) and Esterified Rosins".

*Primary Examiner*—Jenna Davis
*Attorney, Agent, or Firm*—Carolyn V. Peters

[57] ABSTRACT

The invention provides a pressure-sensitive adhesive composition for medical applications comprising a blend of at least two components comprised of about 5 to about 95% by weight of a first component comprised of at least one acrylic pressure-sensitive adhesive and about 5 to about 95% by weight of a second component comprised of either (a) at least one elastomer with a tackifying resin, or (b) at least one thermoplastic elastomer, wherein the resulting pressure-sensitive adhesive demonstrates a $T_0$ of at least 1 N/dm and a $T_{48}$ of less than 12 N/dm when adhered to skin. The pressure-sensitive adhesive composition is prepared either in the presence of a solvent or is alternatively prepared by melt blending. A method of preparing such an adhesive is also disclosed.

23 Claims, No Drawings

PRESSURE-SENSITIVE ADHESIVE SUITABLE FOR SKIN AND METHOD OF PREPARING

Related patent applications entitled Pressure-Sensitive Adhesive, Ser. No. 08/578,010, Pressure-Sensitive Adhesive, Ser. No. 08/577,603; and Adhesive Tape and Method of Making, Ser. No. 08/577,855; all filed on the same date as this application are incorporated herein by reference.

FIELD OF THE INVENTION

The invention relates to pressure-sensitive adhesives. The invention particularly relates to pressure-sensitive adhesives suitable for use on skin.

BACKGROUND

Pressure-sensitive adhesive tapes have been used for more than half a century for a variety of marking, holding, protecting, sealing and masking purposes. Pressure-sensitive adhesive tapes comprise a backing, or substrate, and a pressure-sensitive adhesive. Pressure-sensitive adhesives are materials which adhere with no more than applied finger pressure and are aggressively and permanently tacky. Pressure-sensitive adhesives require no activation other than the finger pressure, exert a strong holding force and should be removable from a smooth surface without leaving a residue.

Adhering to skin presents challenges to adhesive manufacturers due to the inherent variability of the properties of skin. Adhesion to skin is dependent upon many factors. These factors include but are not limited to the environment in which the recipient is located. For instance, adhesion to skin will vary on the same person depending upon the humidity. If the same person were tested for skin adhesion using a given adhesive in different climates, different adhesion results would be obtained depending upon if the person were located in an arid versus in a humid environment. Skin varies from individual to individual. One person may have extremely dry skin to the point of eczema whereas another person may have oily skin. As well as varying from individual to individual, skin properties may vary on a given individual depending upon the location. For instance, skin located on a hand may be considerably drier than skin located on a back or face. Therefore, it is very difficult to manufacture a skin adhesive which is suitable for the environmental and for the individual variabilities.

Adhesive composition and performance is also dependent upon the intended use of the adhesive. Some uses require a gentle tape whereas other uses require an aggressive tape. If an adhesive is adhered to a sensitive area of the body a gentle tape is used. However, if it is critical that the adhesive remain adhered for an extended period of time or if the adhesive is adhered to an area which is very mobile, a more aggressive adhesive is used. The term "gentle" adhesive generally refers to an adhesive for which the adhesion does not substantially build over time. The term "aggressive" adhesive refers to an adhesive which has a substantial resistance to lifting or peeling.

Medical adhesives are generally used in wound dressings, surgical drapes, bandages and tapes. These items are generally constructed of a backing coated with an adhesive. A liner may or may not be used to protect the adhesive. The performance of the adhesive is in part dependent upon the occlusivity of the backing. Backings are generally categorized by their porosity into either nonocclusive or occlusive backings. When nonocclusive backings are used to prepare bandages or the like for medical applications the resulting bandage typically does not adhere well to skin over extended time periods. This probably occurs because the bandage cannot release water vapor which causes retention of moisture and in turn causes the adhesive to lift from the skin.

Conformability and cohesiveness are two inversely related properties which are each important to consider when preparing or selecting adhesives for medical applications. It is desirable for a medical adhesive to conform to the terrain of the skin to which it is adhered. This enhances comfort to the wearer and also ensures a higher initial adhesion to the skin because the adhesive is able to flow into the skin's topography. However, if an adhesive is too conformable it may lack the necessary cohesiveness necessary to remove the dressing with the adhesive intact. If an adhesive lacks cohesive strength the adhesive on a bandage may split upon an attempt to remove the bandage leaving some adhesive residue adhered to the skin and some adhesive removed along with the bandage backing. This is unacceptable to most medical professionals and patients.

Pressure-sensitive adhesives require a delicate balance of viscous and elastic properties which result in a four-fold balance of adhesion, cohesion, stretchiness and elasticity. Pressure-sensitive adhesives generally comprise elastomers which are either inherently tacky, or elastomers or thermoplastic elastomers which are tackified with the addition of tackifying resins. They can be coated in solvent or as water-based emulsions to reduce the material viscosity to a level that is easily applied to a substrate of choice.

Generally, when additives are used to enhance properties of pressure-sensitive adhesives they are required to be miscible with the pressure-sensitive adhesive or to have some common blocks or groups to permit homogeneous blends to form at the molecular level. Pressure-sensitive adhesives have been modified to extend their applicability into new areas. Tackified thermoplastic elastomers have been dissolved in acrylic monomers and subsequently cured. Tackified thermoplastic elastomers have also been added to polymerized acrylic pressure-sensitive adhesives in solvent where each component contains a common segment to permit compatibility. Natural rubber has been added to polymerized acrylic pressure-sensitive adhesives in solvent and subsequently thermally cured. The general purpose is to combine the high shear properties of elastomers with the high tack performance of acrylics to achieve adhesion to both polar and nonpolar surfaces. Further improvements and better balance of properties continue to be sought.

SUMMARY

A medical adhesive is provided which is easily formulated to accommodate skin variabilities, environmental variabilities, and backing variabilities. A medical adhesive is also provided which is easily formulated to accommodate different applications, that is, for either gentle or aggressively adhered products or to vary the initial adhesion and/or the adhesion over extended time periods. Further, a medical adhesive is provided which is conformable enough to exhibit both adequate comfort and adhesion yet exhibits enough cohesive strength so that it is easily removed without leaving a tacky residue.

The present invention provides pressure-sensitive adhesive compositions, and, more particularly, pressure-sensitive adhesive compositions formed from at least two polymeric materials at least one of which is a pressure-sensitive adhesive, and methods for making pressure-sensitive adhesives and articles having pressure-sensitive adhesives components.

The present invention provides a pressure-sensitive adhesive composition for medical applications comprising a blend of at least two components comprised of about 5 to about 95% by weight of a first component comprised of at least one acrylic pressure-sensitive adhesive and about 5 to about 95% by weight of a second component comprised of either (a) at least one elastomer with a tackifying resin, or (b) at least one thermoplastic elastomer, wherein the resulting pressure-sensitive adhesive demonstrates a $T_0$ of at least 1 N/dm and a $T_{48}$ of less than 12 N/dm when adhered to skin. The pressure-sensitive adhesive composition is prepared either in the presence of a solvent or is alternatively prepared by melt blending.

A pressure-sensitive adhesive composition suitable for medical applications is provided. The adhesive is comprised of a blend of at least two components comprised of about 5 to 95 weight percent of a first component comprised of an acrylic pressure-sensitive adhesive and about 5 to 95 weight percent of a second component comprised of either (a) a thermoplastic elastomer, or (b) an elastomer with a tackifying resin, the composition having a morphology comprising at least two distinct domains, a first domain being substantially continuous in nature and the second domain being fibrillose to schistose in nature parallel to a major surface of the adhesive composition within the first domain, wherein the resulting pressure-sensitive adhesive demonstrates a $T_0$ of at least 1 N/dm and a $T_{48}$ of less than 12 N/dm (per Skin Adhesion Test) adhered to skin.

A method for preparing a medical pressure-sensitive adhesive layer is also provided. The method is comprised of the steps of (1) blending at least two components comprised of about 5 to about 95% by weight of a first component comprised of at least one acrylic pressure-sensitive adhesive and about 5 to about 95% by weight of a second component comprised of either (a) at least one elastomer with a tackifying resin, or (b) at least one thermoplastic elastomer, and (2) coating the adhesive to form a layer, wherein the adhesive demonstrates a $T_0$ of at least 1 N/dm and a $T_{48}$ of less than 12 N/dm when adhered to skin. Such an adhesive layer is prepared either by melt blending the materials under shear or extensional conditions or both and coating by forming and drawing the melt blend to form a pressure-sensitive adhesive composition having a morphology comprising at least two distinct domains, a first domain being substantially continuous in nature and a second domain being fibrillose to schistose in nature parallel to the major surface of the adhesive within the first domain or by solvent blending and knife coating.

A method for preparing a medical pressure-sensitive adhesive is provided which comprises solvent blending at least two components comprised of about 5 to about 95% by weight of a first component comprised of at least one acrylic pressure-sensitive adhesive and about 5 to about 95% by weight of a second component comprised of either (a) at least one elastomer with a tackifying resin, or (b) at least one thermoplastic elastomer, wherein the resulting pressure-sensitive adhesive demonstrates a $T_0$ of at least 1 N/dm and a $T_{48}$ of less than 12 N/dm when adhered to skin.

A pressure-sensitive medical adhesive article is provided which comprises a backing, a pressure-sensitive adhesive composition comprising a blend of at least two components comprised of about 5 to 95 weight percent of a first component comprised of an acrylic pressure-sensitive adhesive and about 5 to 95 weight percent of a second component comprised of either (a) at least one thermoplastic elastomeric material or (b) at least one elastomeric material with a tackifying resin; wherein the resulting adhesive article demonstrates a $T_0$ of at least 1 N/dm and a $T_{48}$ of less than 12 N/dm when adhered to skin according to the Skin Adhesion Test as defined herein.

The pressure-sensitive adhesives of the present invention are useful in such applications as medical tapes, wound dressings, bandages, surgical drapes and the like. By proper selection of the polymeric materials, a variety of desirable end use properties can be designed into the adhesive.

DETAILED DESCRIPTION OF THE INVENTION

Acrylic pressure-sensitive adhesives generally have a glass transition temperature of about −20° C. or less and may comprise from 100 to 80 weight percent of a $C_3$–$C_{12}$ alkyl ester component such as, for example, isooctyl acrylate, 2-ethyl-hexyl acrylate and n-butyl acrylate and from 0 to 20 weight percent of a polar component such as, for example, acrylic acid, methacrylic acid, ethylene vinyl acetate, N-vinyl pyrrolidone and styrene macromer. Preferably, the acrylic pressure-sensitive adhesives comprise from 0 to 20 weight percent of acrylic acid and from 100 to 80 weight percent of isooctyl acrylate. The acrylic pressure-sensitive adhesives may be self tacky or tackified. Useful tackifiers for acrylics are rosin esters such as FORAL™ 85, available from Hercules, Inc. of Wilmington, Del., aromatic resins such as PICCOTEX™ LC-55WK, available from Hercules, Inc. aliphatic resins such as ESCOREZ™ 1310LC, available from Exxon Chemical Co of Houston, Tex.

The second component of the pressure-sensitive adhesive compositions of the present invention is either (a) a thermoplastic elastomeric material, or (b) an elastomeric material with a tackifier, which is solvent or melt blended with the acrylic pressure-sensitive adhesive. The material is selected such that it is sufficiently incompatible with the pressure-sensitive adhesive at the use temperature to result in the pressure-sensitive adhesive composition having at least two distinct domains. Of course, more than one second component may be combined with the pressure-sensitive adhesive. The second component may or may not also be a pressure-sensitive adhesive.

Thermoplastic elastomeric materials are generally defined as materials which form at least two phases at 21° C., have a glass transition temperature greater than 50° C. and exhibit elastic properties in one of the phases. Thermoplastic elastomeric materials useful in the present invention include, for example, linear, radial, star and tapered styrene-isoprene block copolymers such as KRATON™ D 1107P, available from Shell Chemical Co. of Houston, Tex. and EUROPRENE™ SOL TE 9110, available from EniChem Elastomers Americas, Inc. of Houston, Tex. linear styrene-(ethylene-butylene) block copolymers such as KRATON™ G1657, available from Shell Chemical Co., linear styrene-(ethylene-propylene) block copolymers such as KRATON™ G1657X, available from Shell Chemical Co., linear, radial, and star styrene-butadiene block copolymers such as KRATON™ D 1118X, available from Shell Chemical Co. and EUROPRENE™ SOL TE 6205, available from EniChem Elastomers Americas, Inc., polyetheresters such as HYTREL™G3548, available from DuPont and poly-α-olefin-based thermoplastic elastomeric materials such as those represented by the formula —(CH$_2$ CHR), where R is an alkyl group containing 2 to 10 carbon atoms and poly-α-olefins based on metallocene catalysis such as ENGAGE™ EG8200, an ethylene/poly-α-olefin copolymer available from Dow Plastics Co. of Midland, Mich.

Elastomeric materials are materials which generally form one phase at 21° C., have a glass transition temperature less than about 0° C. and exhibit elastic properties. Elastomeric materials useful in the present invention include, for example, natural rubbers such as CV-60, a controlled viscosity grade, and SMR-5, a ribbed smoked sheet rubber; butyl rubbers, such as Exxon Butyl 268 available from Exxon Chemical Co.; synthetic polyisoprenes such as CARIFLEX™IR309, available from Royal Dutch Shell of Netherlands and NATSYN™ 2210, available from Goodyear Tire and Rubber Co.; ethylene-propylenes; polybutadienes; polyisobutylenes such as VISTANEX™ MM L-80, available from Exxon Chemical Co.; and styrene-butadiene random copolymer rubbers such as AMERIPOL™ 1011A, available from BF Goodrich of Akron, Ohio.

These thermoplastic elastomeric or elastomeric materials can be modified with tackifying resins or plasticizers to lower their melt viscosity to facilitate the formation of fine dispersions, with the smallest phase dimension preferably less than about 20 microns when blended with the acrylic pressure-sensitive adhesive. Tackifying resins or plasticizers useful with the elastomeric materials or the thermoplastic elastomeric materials are preferably miscible at the molecular level, i.e., soluble in, any or all of the polymeric segments of the elastomeric material or the thermoplastic elastomeric material. The tackifying resins or plasticizers may or may not be miscible with the acrylic pressure-sensitive adhesive. The tackifying resin, when present generally comprises about 5 to 300 parts by weight, more typically up to about 200 parts by weight, based on 100 parts by weight of the elastomeric material or the thermoplastic elastomeric material. Examples of tackifiers suitable for the invention include but are not limited to liquid rubbers, hydrocarbon resins, rosin, natural resins such as dimerized or hydrogenated balsams and esterified abietic acids, polyterpenes, terpene phenolics, phenol-formaldehyde resins, and rosin esters. Examples of plasticizers include but are not limited to polybutene, paraffinic oils, petrolatum, and certain phthalates with long aliphatic side chains such as ditridecyl phthalate.

In addition, other additives such as pigments, fillers, and antioxidants may be used in the pressure-sensitive adhesive composition. Examples of fillers include but are not limited to inorganic fillers such as zinc oxide, alumina trihydrate, talc, titanium dioxide, aluminum oxide and silica. Other additives such as amorphous polypropylene or various waxes may also be used. Pigments and fillers may be incorporated into the adhesive composition in order to manipulate the properties of the adhesive according to its intended use. For instance, very fine pigments increase cohesive strength and stiffness, reduce cold flow, and also reduce tack. Platy pigments such as mica, graphite, and talc are preferred for acid and chemical resistance and low gas permeability. Coarser pigments increase tack. Zinc oxide increases tack and cohesive strength. Aluminum hydrate, lithopone, whiting, and the coarser carbon blacks such as thermal blacks also increase tack with moderate increase in cohesivity. Clays, hydrated silicas, calcium silicates, silicoaluminates, and the fine furnace and thermal blacks increase cohesive strength and stiffness. Radiation crosslinkers such as benzophenone, derivatives of benzophenone, and substituted benzophenones such as acryloyloxybenzophenone may also be added to the adhesive compositions of the invention. Finally, antioxidants may be used to protect against severe environmental aging caused by ultraviolet light or heat. Antioxidants include, for example, hindered phenols, amines, and sulfur and phosphorous hydroxide decomposers. One skilled in the art will recognize that certain situations call for special types of plasticizers, tackifiers, pigments, fillers, crosslinkers and/or antioxidants and selection can be critical to the performance of the adhesive.

The acrylic pressure-sensitive adhesive and the thermoplastic elastomeric material or elastomeric material are blended and coated using melt extrusion techniques or by solvent coating. Mixing can be done by any method that results in a substantially homogeneous distribution of the acrylic pressure-sensitive adhesive and the thermoplastic elastomeric material or elastomeric material.

If a hot melt coating is desired the blend of the acrylic pressure-sensitive adhesive and the thermoplastic elastomeric material or tackified elastomeric material is prepared by melt mixing the components in the molten or softened state using devices that provide dispersive mixing, distributive mixing, or a combination of dispersive and distributive mixing. Both batch and continuous methods of blending may be used. Examples of batch methods include Brabender™ or Banbury™ internal mixing, and roll milling. Examples of continuous methods include single screw extruding, twin screw extruding, disk extruding, reciprocating single screw extruding, and pin barrel single screw extruding. The continuous methods can include both distributive elements such as cavity transfer elements such as CTM™, available from RAPRA Technology, Ltd., Shrewsbury, England, pin mixing elements, and static mixing elements and dispersive elements such as Maddock mixing elements or Saxton mixing elements.

After the hot melt mixing step, the softened or molten acrylic pressure-sensitive adhesive and thermoplastic elastomeric or tackified elastomeric material blend is formed into coatings which have a morphology such that the pressure-sensitive adhesive forms a substantially continuous domain and the thermoplastic tackified elastomeric material or the elastomeric material forms a domain which is fibrillose to schistose in nature by processes that involve either shear or extensional deformations or both. When a tackifying agent is blended with the thermoplastic elastomeric material or the elastomeric material such that this too is now an adhesive material, then either adhesive domain may be continuous or the domains may be co-continuous. These processes may be either batch or continuous.

An example of a batch process is the placement of a portion of the blend between the desired substrate to be coated and a release liner, pressing this composite structure in a heated platen press with sufficient temperature and pressure to form a pressure-sensitive coating of the desired thickness and cooling the resulting coating.

Continuous forming methods include drawing the pressure-sensitive adhesive composition out of a film die and subsequently contacting a moving plastic web or other suitable substrate. A related continuous method involves extruding the pressure-sensitive adhesive composition and a coextruded backing material from a film die and subsequently cooling to form a pressure-sensitive adhesive tape. Other continuous forming methods involve directly contacting the pressure-sensitive adhesive blend to a rapidly moving plastic web or other suitable substrate. In this method, the pressure-sensitive adhesive blend can be applied to the moving web using a die having flexible die lips such as a reverse orifice coating die. After forming, the pressure-sensitive adhesive coatings are solidified by quenching using both direct methods, such as chill rolls or water baths, and indirect methods, such as air or gas impingement.

For hot melt mixing, preferably, each of the polymeric components has similar melt viscosity. The ability to form a finely dispersed morphology is related to the viscosity ratio and concentration of the components. The shear viscosity is determined using capillary rheometry at a shear rate approximating extrusion blending conditions, i.e., $100s^{-1}$ and 175° C. When a higher viscosity thermoplastic elastomeric material is present as the minor component, the viscosity ratio of the minor component to the major component is preferably less than about 20:1, more preferably less than about 10:1. For pressure-sensitive adhesive compositions comprising acrylate adhesive materials and thermoplastic materials, when a lower viscosity polymeric material is present as the minor component, viscosity ratios of the minor component to the major component are preferably greater than about 1:10, more preferably greater than about 1:5. For pressure-sensitive adhesive compositions comprising acrylate adhesive and tackified elastomeric materials the viscosity ratios are 5:1, 2:1, 1:30, and 1:10 respectively. The melt viscosities of individual polymeric materials may be altered by the addition of plasticizers, tackifiers or solvents or by varying mixing temperatures. If the use of solvent is required, the solvent is preferably removed before the extrusion coating step to prevent foaming.

It is also preferable that at least one of the polymeric materials be easily extended in the melt blending and coating operations to form a finely dispersed morphology with domains which are fibrillose to schistose, e.g., forming sheets, ribbons, fibers, ellipsoids or the like, oriented in the web formation direction in the substantially continuous or co-continuous domain of the other polymeric material. Sufficient interfacial adhesion between the acrylic pressure-sensitive adhesive component and the thermoplastic elastomeric component preferably exists to withstand the shear and extensional deformation present during the forming step and to promote formation of a continuous film.

If none of the polymeric materials can be easily extended in the melt blending and coating or sufficient interfacial adhesion is not present, a pressure-sensitive adhesive coating may be produced which has gross discontinuities and is grainy in texture. Through use of suitably selected conditions of mixing, closeness of melt viscosities, and shear/stretch conditions during extrusion, the thickness of the fibrillose to schistose domains can be made sufficiently thin that delamination from the substantially continuous or co-continuous domain will not occur. Preferably, the thickness of the fibrillose to schistose domains is less than about 20 microns, more preferably less than about 10 microns, and most preferably less than about 1 micron although the size will vary depending on specific blends, i.e., polymer types, concentration, viscosity, and the like.

The acrylic pressure-sensitive adhesive and the thermoplastic elastomeric material or elastomeric material are optionally blended and coated using solvent blending and solvent coating techniques. Viscosity ratios of the acrylic pressure-sensitive adhesive and either the thermoplastic elastomeric component or the tackified elastomeric component do not apply if solvent coating techniques are used. However, the components should be substantially soluble in the solvents used. Mixing can be done by any method that results in a substantially homogeneous distribution of the acrylic pressure-sensitive adhesive and the thermoplastic elastomeric material or tackified elastomeric material. The blend of the acrylic pressure-sensitive adhesive and the thermoplastic elastomeric material or elastomeric material is prepared by combining the components in the presence of solvent and mixing the components.

Once the solvent blended adhesive composition is obtained, the adhesive is solvent coated by such methods as, for example, knife coating, roll coating, gravure coating, rod coating, curtain coating, and air knife coating. The adhesive coating is then dried to remove the solvent. Preferably the adhesive coating is subjected to increased temperatures such as supplied by an oven in order to expedite the drying of the adhesive.

The adhesive of the invention is useful to prepare medical adhesive articles such as surgical tapes and drapes, bandages, athletic tapes, wound dressings and the like. The adhesive may be coated onto any backing suitable for medical uses including occlusive (substantially non-breathable) and non-occlusive backings (breathable). Occlusive backings are also known as low porosity backings. Nonlimiting examples of occlusive backings include films, foams and laminates thereof. Nonlimiting examples of non-occlusive backings include woven substrates, nonwoven substrates such as hydroentangled materials or melt blown webs, foams and thermally embossed nonwoven substrates.

This invention is further illustrated by the following examples which are not intended to limit the scope of the invention. In the examples, all parts, ratios and percentages are by weight unless otherwise indicated. The following test methods were used to evaluate and characterize polymeric materials and the pressure-sensitive adhesive compositions produced in the examples.

Skin Adhesion

Skin adhesion was carried out by placing tape samples 2.5 cm wide by 7.5 cm long on the back of a human subject. Each tape was rolled down with one forward and one reverse pass using a 2 Kg roller moved at a rate of about 30 cm/min. Adhesion to the skin was measured as the peel force required to remove the tape at 180 degree angle at a 15 cn/min. rate of removal. Adhesion was measured immediately after initial application ($T_0$) and after 24 hours (T24) or 48 hours ($T_{48}$). Preferred skin adhesives generally exhibit a $T_0$ of between about 50 to 100 grams (1.9 to 3.8 N/dm) and a $T_{24}$ of between about 150 to 300 grams (5.8 to 11.5 N/dm). Results of 9 tests were averaged.

Skin Adhesion Lift Test

When the aged skin adhesion test was performed, the tape sample was examined for the amount of area that was lifted (released) from the skin prior to removal of the tape and ratings were given as:
0 no visible lift
1 lift only at edges of tape
2 lift over 1% to 25% of test area
3 lift over 25% to 25% of test area
4 lift over 50% to 75% of test area
5 lift over 75% to 100% of test area
Results of 9 tests were averaged. Preferred skin adhesives will generally exhibit an average rating below about 2.5.

Skin Residue Test

When the aged skin adhesion test was performed, the skin underlying the tape sample was visually inspected to determine the amount of adhesive residue on the skin surface and was rated as:
0 no visible residue
1 residue only at edges of tape
2 residue covering 1% to 25% of test area
3 residue covering 25% to 50% of test area
4 residue covering 50% to 75% of test area
5 residue covering 75% to 100% of test area
Results of 9 tests were averaged. Preferred skin adhesives will generally exhibit an average rating below 2.5.

EXAMPLE 1

Example 1 demonstrates that adhesive blends comprised of acrylate adhesive and thermoplastic elastomers perform well when coated on non-occlusive (breathable) backings and when adhered to skin. The adhesive blends perform well whether they are prepared by hot melt blending (Example 1A) or by solvent blending (Example 1B) methods.

The following pressure-sensitive acrylate adhesive was used to prepare the blend adhesives of Examples 1A and 1B.

Acrylate Pressure Sensitive Adhesive Preparation

An acrylic pressure-sensitive adhesive (designated hereafter as "acrylate adhesive A") was prepared in accordance with U.S. Pat. No. 4,833,179 (Young, et al.) in the following manner: A two liter split reactor equipped with condenser, thermowell, nitrogen inlet, stainless steel motordriven agitator, and a heating mantle with temperature control was charged with 750 g deionized water, to which was added 2.5 g of zinc oxide and 0.75 g hydrophilic silica (CAB-O-SIIL C(M) EH-5, available from Cabot Corp. of Tuscola, Ill.) and was heated to 55 degrees C. while purging with nitrogen until the zinc oxide and silica were thoroughly dispersed. At this point, a charge of 480 g isooctyl acrylate, 20 g methacqlic acid, 2.5 g initiator (VAZO™ 64, available from DuPont Co.) and 0.5 g isooctyl thioglycolate chain transfer agent was then added to the initial aqueous mixture while vigorous agitation (700 rpm) was maintained to obtain a good suspension. The reaction was continued with nitrogen purging for at least 6 hours, during which time the reaction was monitored to maintain a reaction temperature of less than 70 degrees C. The resulting pressure-sensitive adhesive was collected and machine pressed to at least 90% solids by weight.

An acrylic pressure-sensitive adhesive (designated hereafter as "acrylate adhesive B") using an acrylate pressure-sensitive adhesive (95 weight percent isooctyl acrylate/5 weight percent acrylic acid, water emulsion polymerized, shear viscosity 150 Pa-s, prepared according to U.S. Pat. No. RE 24,906 (Ulrich) and drum dried.

1A. Hot Melt Coated Acrylate/Thermoplastic Elastomer Adhesive Blends Coated on Non-Occlusive Backings A hot melt pressure-sensitive adhesive was prepared using the acrylate adhesive A and a thermoplastic elastomer which was a Kraton T 1107 adhesive (Kraton™ 1107 rubber/Escorez™ 1310 LC tackifier 50/50) of various ratios by melt blending. The blend adhesive was prepared by feeding the acrylate adhesive into a pin barrel mixer.

The acrylate/adhesive was added through the screw feeder of a 8.9 cm diameter screw feeder and a 8.9 cm diameter screw pin barrel mixer used for the mixing of the adhesives from the French Oil Mill Machinery Co., Piqua, Ohio. The precompounded KRATON™ 1107 (TPE) adhesive was delivered via a gear pump from an unloader system # C57435 from Graco, Inc. of Plymouth, Mich. between zone 1 and zone 2 of the mixing screw. Water was injected at a 1% level before coating after zone 4. A gear pump attached to the output end of the pin barrel mixer by a heated hose delivered the blend composition to the die. A 28 cm wipe film die was used to coat the various adhesives and film backings. Line speed was varied to give coating thickness of 21 microns.

The following output rates were used for the various ratios coated on different backings:

| Acrylate/TPE 1107 Blend Adhesive | | | |
|---|---|---|---|
| 0/100 | 15.9 Kg/hr TPE | | |
| 25/75 | 3.8 Kg/hr Acrylate | / | 11.3 Kg/hr TPE |
| 50/50 | 11.3 Kg/hr Acrylate | / | 11.3 Kg/hr TPE |
| 75/25 | 11.3 Kg/hr Acrylate | / | 3.8 Kg/hr TPE |
| 100/0 | 11.3 Kg/hr Acrylate | | |

The temperature ranges for the zones are given below for the various ratios of adhesive blends. In all cases the die temperature was kept at 160° C.

| | | | °C. |
|---|---|---|---|
| 0/100 | Zone | 1 | 108 |
| | | 2 | 131 |
| | | 3 | 116 |
| | | 4 | 147 |
| 25/75 | Zone | 1 | 124–125 |
| | | 2 | 122–123 |
| | | 3 | 121–123 |
| | | 4 | 128–131 |
| 50/50 | Zone | 1 | 126–129 |
| | | 2 | 125 |
| | | 3 | 132–137 |
| | | 4 | 131–138 |
| 75/25 | Zone | 1 | 106–111 |
| | | 2 | 123–128 |
| | | 3 | 111–127 |
| | | 4 | 123–144 |
| 100/0 | Zone | 1 | 105–109 |
| | | 2 | 128–130 |
| | | 3 | 116–135 |
| | | 4 | 142–152 |

The adhesive blends coated onto a nonwoven rayon fiber a non-occlusive backing to prepare samples 1A–1E. The backing was formed by first passing 2.5 to 5 cm long staple 1.5 denier viscose-rayon textile fibers through a twin cylinder card (available from Spinnbau GmbH, Bremen, Germany) to form a fluffy fiber web with a fiber weight of between 41 g/m² and 54 g/m². The fluffy fiber web was simultaneously compacted to a tissue-like condition and sized by being fed through the nip of a pair of horizontal squeeze rolls, the lower one of which dips in an aqueous bath of fiber-binding rubbery acrylate sizing latex (like RHOPLEX™ B-15, available from Rohm-Haas Co. diluted with water to provide a size weight approximately equal to the weight of the fiber); and then dried.

Samples 1A–1E were tested for skin adhesion properties including initial adhesion, adhesion after 48 hours, lift and the amount of adhesive residue remaining after removal of the sample (residue). Results are shown in the table below.

| Sample # | Acrylate/TPE Ratio | $T_0$ N/dm | $T_{48}$ N/dm | Lift | Residue |
|---|---|---|---|---|---|
| 1A | 100/0 | 1.9 | 6.1 | 0.3 | 0.4 |
| 1B | 75/25 | 2.3 | 8.3 | 0.4 | 0.3 |
| 1C | 50/50 | 2.8 | 6.7 | 0.9 | 0.4 |
| 1D | 25/75 | 2.5 | 3.9 | 1.2 | 0.0 |
| 1E | 0/100 | 1.1 | 2.3 | 3.2 | 0.0 |

Samples 1A through 1E show that the blends of acrylate and thermoplastic adhesive blends on samples (1B through 1D) demonstrate usually higher $T_0$ and $T_{48}$ values than the pure adhesive components used on Samples 1A through 1E. The blends showed a synergistic effect and not an additive effect. The skin adhesion properties are determined by the ratio of the components.

1B. Solvent Coated Acrylate/Thermoplastic Elastomer (TPE) Adhesive Bends Coated On Non-Occlusive Backings Batch solutions of the acrylate adhesive and thermoplastic elastomer were prepared in the following manner. Acrylate adhesive A was dissolved in a heptane/isopropyl alcohol 90/10 mixture at 25% solids in a 3.8 liter jar. The thermoplastic elastomer Kraton™ 1107 and tackifier Escorez™ 1310 LC at a 50/50 mix were dissolved in toluene at 50% solids in a 3.8 liter glass jar. Each batch solution was mixed on a roller mixer overnight at room temperature (approximately 21° C.).

Various adhesive blends containing different ratios of the acrylate and thermoplastic elastomer components were prepared by combining the appropriate amounts of acrylate adhesive and Kraton adhesive blends in 0.9 liter glass jars and sealed with lids. The combinations were allowed to mix on a roll mixer overnight at room temperature. Process conditions are listed in the Table below.

The resulting adhesives were coated onto silicone liner as available from Daubert Coated Products, Inc. of Culman, Ala. The adhesive was subjected to a dual oven system to remove solvent from the adhesives. The first oven temperature was at 36° C. and the second oven temperature was at 135 degrees C. After drying, a non-occlusive backing was laminated onto the adhesives at a coating thickness of 21 microns. The backing was formed as in Example 1A. The liner was left in place to prevent blocking of the tapes.

| Tape # | Acrylate/TPE Ratio | solids % | orifice microns | speed m/min |
|---|---|---|---|---|
| 1F | 100/0 | 25 | 179 | 1.2 |
| 1G | 75/25 | 31 | 140 | 1.2 |
| 1H | 50/50 | 38 | 127 | 1.2 |
| 1I | 25/75 | 44 | 127 | 1.2 |
| 1J | 0/100 | 50 | 76 | 1.2 |

Samples 1F–1J were tested for skin adhesion properties including initial adhesion, adhesion after 48 hours, lift and the amount of adhesive residue remaining after removal of the sample (residue). MICROPORE™ Brand adhesive tape available from 3M of St. Paul, Minn. was tested as a Competitive Sample. Results are shown in the table below.

| Tape # | M2000/Kraton 1107 Ratio | $T_0$ N/dm | $T_{48}$ N/dm | Lift | Residue |
|---|---|---|---|---|---|
| 1F | 100/0 | 1.7 | 5.8 | 0.7 | 0.5 |
| 1G | 75/25 | 1.8 | 6.8 | 0.4 | 0.4 |
| 1H | 50/50 | 1.9 | 6.0 | 0.3 | 0.2 |
| 1I | 25/75 | 3.1 | 5.2 | 1.5 | 2.3 |
| 1J | 0/100 | 3.2 | 4.5 | 1.6 | 1.9 |
| Competitive Sample | Micropore ™ | 1.2 | 5.3 | 0.5 | 0.2 |

Samples 1F through 1J demonstrate that the blend adhesives comprised of acrylate and thermoplastic elastomer (Samples 1G and 1H) offer usually higher $T_{48}$ properties than the pure adhesive components (Samples 1F and 1J). The blends showed a synergistic effect and not an additive effect. The skin adhesion properties are determined by a ratio of the components in both $T_0$ and $T_{48}$.

A competitive tape Sample, MICROPORE™ Brand Adhesive Tape, demonstrates that skin adhesion properties of both the hot melt and solvent coated adhesive compositions on non-occlusive backings are competitive with a commercially available tape.

Both the hot melt and the solvent coated pressure-sensitive adhesive blends perform well for skin adhesion. This is apparent due to the satisfactory initial adhesion, the satisfactory adhesion after 48 hours and the limited lift demonstrated by the samples. Additionally, the residue remaining on the skin after removal of the adhesive was usually low. The skin adhesion properties of a given adhesive are determined by the component ratios in the adhesive composition.

EXAMPLE 2

Example 2 demonstrates that pressure-sensitive adhesive blends comprised of acrylate adhesives and thermoplastic elastomer blends perform well when coated on occlusive backings and when adhered to skin. This is true whether the adhesives are hot melt coated (Example 2A) or solvent coated (Example 2B).

2A. Hot Melt Coated Acrylate/Thermoplastic Elastomer Adhesive Blends Coated on Occlusive Backings The adhesive prepared in Example 1A above was coated onto an occlusive backing using the same coating method and processing conditions described above. The occlusive backing used was a 76 micron thick low density polyethylene film made with NA-964-085 polyethylene resin from Quantum Chemical Co. of Cincinnati, Ohio.

Samples 2A–2E were tested for skin adhesion properties including initial adhesion, adhesion after 48 hours, lift and the amount of adhesive residue remaining after removal of the sample (residue). Results are shown in the table below. The coating thickness was 39 microns.

| Tape # | Acrylate/TPE Ratio | $T_0$ N/dm | $T_{48}$ N/dm | Lift | Residue |
|---|---|---|---|---|---|
| 2A | 100/0 | 2.2 | 3.5 | 0.8 | 1.2 |
| 2B | 75/25 | 2.8 | 3.2 | 0.9 | 1.1 |
| 2C | 50/50 | 2.5 | 1.4 | 2.0 | 0.5 |
| 2D | 25/75 | 2.6 | 0.3 | 4.8 | 0.0 |
| 2E | 0/100 | 2.4 | 0.2 | 4.0 | 0.0 |

Samples 2A through 2E demonstrate that the adhesive blends of acrylate and thermoplastic elastomers (Samples 2B through 2D) offer higher $T_0$ values than the pure components (Samples 2A and 2E). The blends show a synergistic effect and not an additive effect. The skin adhesion for both $T_0$ and $T_{48}$ is determined by the ratio of components.

The effect of the backing is evident in the $T_{48}$ values by comparing non-occlusive backing samples (Samples 1A through 1E) with occlusive backing samples (Samples 2A through 2E). The occlusive backing samples show a decreased $T_{48}$ skin adhesion value. Without being bound by theory it is believed that retaining water vapor or water next to the adhesive reduces the $T_{48}$ values.

The effect the backing has on adhesion values is not as evident when examining the $T_0$ values by comparing Samples 1A–1E (non-occlusive backing) with Samples 2A–2E (occlusive backing). It is believed that with initial adhesion ($T_0$) the water vapor has not built next to the adhesive to the extent that it has a large effect on the adhesion values.

The $T_0$ values of both the non-occlusive and occlusive backing samples show the improved skin adhesion of the blends as compared to the pure components.

2B. Solvent Coated Acrylate/Thermoplastic Elastomer Adhesive Bends Coated on Occlusive Backing The adhesive prepared in Example 1B above was coated onto an occlusive backing using the same coating method as described above except that processing conditions for coating samples 2F–2J are identified in the table below. The occlusive backing used was as in Example 2A.

| Tape # | Acrylate/ TPE Ratio | solids % | thickness microns | orifice microns | speed m/min | Oven zone 1 C | Oven zone 2 C |
|---|---|---|---|---|---|---|---|
| 2F | 100/0 | 25 | 39 | 316 | 1.1 | 34 | 135 |
| 2G | 75/25 | 31 | 39 | 279 | 1.1 | 34 | 135 |
| 2H | 50/50 | 38 | 39 | 203 | 1.1 | 34 | 135 |
| 2I | 25/75 | 44 | 39 | 152 | 1.1 | 35 | 135 |
| 2J | 0/100 | 50 | 39 | 112 | 1.1 | 35 | 135 |

Samples 2F–2J were tested for skin adhesion properties including initial adhesion, adhesion after 48 hours, lift and the amount of adhesive residue remaining after removal of the sample (residue). BLENDERM™ Brand adhesive tape available from 3M of St. Paul, Minn. was tested as a Competitive Sample. Results are shown in the table below.

| Sample # | Acrylate/TPE Ratio | $T_0$ N/dm | $T_{48}$ N/dm | Lift | Residue |
|---|---|---|---|---|---|
| 2F | 100/0 | 2.6 | 3.3 | 0.8 | 1.0 |
| 2G | 75/25 | 2.8 | 2.9 | 1.1 | 1.3 |
| 2H | 50/50 | 2.5 | 1.9 | 0.9 | 0.6 |
| 2I | 25/75 | 2.3 | 0.3 | 4.5 | 0.0 |
| 2J | 0/100 | 2.6 | 0.2 | 4.9 | 0.0 |
| Competitive Sample | Blenderm ™ | 3.1 | 0.8 | 2.8 | 0.3 |

The solvent coated Samples (2F–2J) had slightly higher $T_0$ and slightly lower $T_{48}$ values than the hot melt coated Samples (1F through 1J), however, the differences are not significant.

The $T_{48}$ values show the effect of an occlusive backing as described above. When comparing Samples 2F–2J (solvent coated on occlusive backing) to Samples 1F–1J (solvent coated on non-occlusive backing), it is apparent that the 48 hour skin adhesion is reduced for the occlusive backing. Even the thicker coating of adhesive on the occlusive backing did not help to increase the $T_{48}$ values of the occlusive backing samples.

When comparing $T_{48}$ between hot melt coated samples (2A–2E) and solvent coated samples (2F–2J), the effect of changing the ratios of the components is apparent. That is, the blend adhesives perform between the pure components. Both hot melt and solvent behave in a similar manner.

A competitive tape Sample, BLENDERM™ demonstrates that both hot melt and solvent coated adhesive compositions of the invention are comparable, when coated on occlusive backings to commercially available medical tape.

EXAMPLE 3

Example 3 illustrates that a cloth/polymeric composite backing is useful as a non-occlusive backing for preparing tape constructions for adhering to skin. Example 3 illustrates that different methods of preparing and coating the adhesive blends of the invention are useful when preparing adhesives for applying to skin. The cloth/polymer composite backing used to prepare the tape samples of Examples 3A, 3B and 3C was prepared as follows.

Backing Preparation

The cloth/polymer composite comprised of ENGAGE™ 8200 (a polyolefin available from Dow Plastics Co.) was extrusion coated onto 44×36 woven cloth (available from Burcott Mills). White backing was produced by dry blending 1 part of 50:50 titanium dioxide in low density polyethylene (available as PWC00001 from Reed Spectrum, Holden Mass.) with 3 parts ENGAGE™ 8200; forming pigmented pellets by melt mixing the blend in a 40 mm twin screw extruder (available from Berstorff) at 200° C. and extruding and pelletizing the strands; dry blending the pigmented pellets with more unpigmented ENGAGE™ 8200 in a ratio of 1:25; melt mixing the blend and feeding the blend at approximately 270 g/min into the feed throat of a 6.35 cm diameter Standard Model #N9485 single screw extruder (available from Davis Standard, Paucatuck, Conn.) at 204° C. and extruding a 6.5 micron thick film onto the cloth with the cast roll temperatures set at 93° C. to form a composite and passing the composite through the nip of two horizontal rolls at pressures of 350N per lineal cm (200 pound per in) at approximately 1.1 m/min.

3A. Hot Melt Acrylate/Thermoplastic Elastomer (TPE) Adhesive Blend Coated onto Cloth/Polymer Composite Backing An adhesive containing a blend of an acrylate adhesive A and thermoplastic elastomeric adhesive was prepared by melt blending the acrylate adhesive A with a thermoplastic elastomer adhesive (prepared by preblending 50 parts thermoplastic elastomeric block copolymer KRATON™ D1107P available from Shell Chemical Co of Houston, Tex., 1.0 parts antioxidant IRGANO™ 1076, available from Ciba-Geigy of Hawthorne, N.Y. and 50 parts tackifying resin ESCOREZ™ 1310 LC available from Exxon Chemicals of Houston, Tex.) at a ratio of 50:50 with the process described in Example 1A. The composition was coated onto the polymer/cloth composite described above. The backing sample was coated with adhesive at a thickness of 57 microns. 3M Brand Cloth Adhesive Tape available from 3M of St. Paul, Minn. and ZONAS POROUS™ brand tape available from Johnson & Johnson Medical, Inc. of Arlington, Tex. were used as Competitive Samples. The resulting tape sample and the competitive tapes were tested for skin adhesion. Results are shown below:

Skin Adhesion Results - Sample Obtained from Hot Melt Coating Acrylate/TPE Adhesive Blend Onto Cloth/Polymer Composite Backing

| Sample # | Acrylate/TPE ratio (by weight) | Coating Thickness (microns) | Wet To (N/dm) | T0 (N/dm) | T48 (N/dm) | Lift (1–5) | Residue (1–5) |
|---|---|---|---|---|---|---|---|
| 3A | 50/50 | 57 μm | — | 1.8 | 3.4 | 1.5 | 0.2 |
| 3M Brand | competitive | — | 3.6 | 1.2 | 4.1 | 1.4 | 0.8 |
| J&J Zonas Porous | competitive | — | 2.2 | 0.9 | 3.3 | 1.6 | 0.5 |

3B. Solvent Coated Acrylate/Thermoplastic Elastomer Adhesive Blends Coated onto Cloth/Polymer Composite Backings An adhesive containing a blend of an acrylate adhesive and thermoplastic elastomeric adhesive was prepared by dissolving the acrylate adhesive (described in Example 1 above) in a heptane/isopropyl alcohol 90/10 mix at 25% solids in a 3.8 liter glass jar. The thermoplastic elastomer (KRATON™ 1107) was tackified using ESCOREZ™ 131OLC so that a 50:50 ratio was obtained. The KRATON™/tackifier composition was dissolved in toluene at 50% solids in a 3.8 liter glass jar. Each batch solution was mixed on a roll mixer overnight at room temperature (25 degrees C.). A 50:50 blend ratio was prepared by combining the appropriate amounts acrylate adhesive and KRATON™ adhesive in a 0.9 liter glass jar, sealed with a lid and allowed to mix on a roll mixer overnight at room temperature.

The adhesive was coated on the cloth/polymer composites described above 37.5 solids to produce a coating thickness of 32 micrometers. The coating was accomplished with a 25.4 cm wide knife coater.

The coated sample was then subjected to a dual oven system to remove the solvent in the adhesive. The first oven temperature was at 37.7 degrees C. while the second oven was at 135 degrees C. A liner (Daubert) was inserted before wind-up to ensure the adhesives on the samples would not block on the uncoated backing surface before testing was complete. The resulting tape sample was measured for skin adhesion. Additionally, Zonas Porous brand tape available from Johnson & Johnson Medical, Inc. of Arlington, Tex. and 3M brand Cloth Adhesive Tape available from 3M of St. Paul, Minn. were tested for the same properties for comparative purposes. Results are shown in the table below:

| Sample | T0 (N/dm) | T48 (N/dm) | Lift | Residue |
| --- | --- | --- | --- | --- |
| 3U | 2.1 | 2.7 | 1.5 | 1.0 |
| J&J Zonas | 1.4 | 2.0 | 2.4 | 0.3 |

3C. Hot Melt Acrylate/Thermoplastic Elastomer/Filler Blend Adhesive Coated onto Cloth Polymer Composite Backing An adhesive containing acrylate adhesive A, thermoplastic elastomeric adhesive, and filler were melt blended in a twin screw extruder and hot melt coated directly onto the cloth/polymer laminate. The blend containing acrylate adhesive A/thermoplastic elastomer/tackifying resin/filler at 60/20/20/11.1 parts respectively was prepared by feeding KRATON™ D1107 pellets (Shell Chemical) into barrel 1 of a 30 mm ZSK 30 Werner and Pfleiderer Corp., Ramsey, N.J. twin screw extruder with LID of 45:1, adding a tackifier/filler powder mixture of ESCOREZ™ 1310 LC (Exxon Chemical) and alumina trihydrate (Micral 1500 grade from Solex Industries, Norcross, Ga.) at a ratio of 1.8:1 into barrel 3 of the extruder and feeding the acrylate adhesive (prepared as described above) barrel 8 of the twin screw extruder. The blend was compounded in the extruder at 149 degrees C. at rpm of approximately 400, passed through a screen filter and gear pump located at the end of the extruder at 166 degrees C. and delivered by a heated pipe to a wipe-film coating die maintained at 166 degrees C. Extruder outputs were approximately 2.0 Kg/hr/1.4 cm die width. The adhesive coating had an average thickness of approximately 50 micrometers.

The samples were tested for their adhesion to steel, adhesion to backing, unwind, initial adhesion to skin and after 48 hours, lift and residue. Results are shown in the table below.

| | Hot Melt Acrylate/TPE Filler Properties | | | | | | |
| --- | --- | --- | --- | --- | --- | --- | --- |
| Sample | Adh steel N/dm | Adh backing N/dm | Unwind N/dm | T0 N/dm | T48 N/dm | Lift | Residue |
| 3C | 25 | 12 | 9 | 1.0 | 3.1 | 1.0 | 0.0 |

EXAMPLE 4

Example 4 demonstrates that adhesive blends comprised of acrylate pressure-sensitive adhesive and at least one elastomer perform well when adhered to skin. This is true whether the adhesive blend is prepared by hot melt blending (Example 4A) or by solvent blending (Example 4B).

The following components were used to prepare the adhesive blends of Example 4. Natsyn™ 2210 is an elastomer comprised of synthetic polyisoprene available from Goodyear Tire and Rubber Company of Akron, Ohio. Wingtack™ 95 is a hydrocarbon tackifier also available from Goodyear Tire and Rubber Company. Vistanex™ LM-MH (Flory MW 53,000) and Vistanex™ MM L-80(Flory MW 990,000) are elastomeric polyisobutylenes available from the Exxon Chemical Company of Houston, Tex. Ameripol™ 1011 A is an elastomeric styrene butadiene rubber available from BF Goodrich of Akron, Ohio. Foral™ 85 is a rosin ester tackifier available from Hercules Inc. of Wilmington, Del.

A Warner-Pfeiderer 30 mm ZSK 30 twin screw extruder with an L/D of 37:1 was used to prepare the hot melt blend acrylate/elastomer pressure-sensitive adhesive. The elastomer NATSYN™ 2210 was fed into barrel 2, VISTANEX™ LMMH was fed into barrel 4 and the acrylate adhesive was fed into barrel 6 of the extruder. The extruder zone 1 temperature was 149° C., zone 2 was 161° C., zone 3 was 163° C., zone 4 was 163° C., zone 5 was 163° C., zone 6 was 163° C., die was 163° C. the extrusion rate was 0.32 Kg/hr per cm die width, and the extruder rpm was 299. The barrels were divided as follows: barrel 1 (unheated), barrels 2–3 (zone 1), barrels 4–5 (zone 2), barrels 6–7 (zone 3), barrels 8–9 (zone 4), barrel 10 (zone 5), and barrels 11–12 (zone 6). Line speed was adjusted from 0 to 12.8 m/minute to achieve adhesive target thickness.

4A. Hot Melt Coated Acrylate/Elastomer Adhesive Blends On Non-Occlusive Backings The acrylate/elastomer blend adhesive described above was coated at a thickness of 57 microns onto a backing. The backing was a 180×48 plain weave acetate taffeta cloth, 75 denier fiber in the warp direction, 150 denier fiber in the weft direction as available from Milliken & Co. of Spartanburg, Ga.

Samples 4A–4E were tested for skin adhesion properties including initial adhesion, adhesion after 48 hours, lift and the amount of adhesive residue remaining after removal of the sample (residue).

| Sample # | Acrylate/Elastomer/ Tackifier Ratio | $T_0$ N/dm | $T_{48}$ N/dm | Lift | Residue |
|---|---|---|---|---|---|
| 4A | 100/0/0 | 2.0 | 7.5 | 0.8 | 0.5 |
| 4B | 75/9/16 | 2.4 | 8.4 | 0.7 | 0.6 |
| 4C | 50/19/31 | 2.7 | 8.8 | 0.8 | 0.8 |
| 4D | 25/28/47 | 2.2 | 5.8 | 1.1 | 0.5 |
| 4E | 0/37/63 | 1.6 | 2.3 | 1.5 | 0.3 |

Samples 4A through 4E demonstrate that the adhesive blends of acrylate and elastomer components (Samples 4B through 4D) offer usually higher $T_0$ and $T_{48}$ than the pure components (Samples 4A through 4E). The blends show a synergistic effect and not an additive effect. The skin adhesion $T_0$ and $T_{48}$ is determined by the ratio of the components.

4B. Solvent Coated Acrylate/Elastomer Adhesive Bends On Non-Occlusive Backings

Solvent coated acrylate/elastomer blend pressure-sensitive adhesive tapes were prepared in the following manner. The solvent adhesive blends were first prepared. Acrylate adhesive A was dissolved in a toluene/heptane 90/10 mix ratio at 20% solids in a gallon jar. Elastomers Natsyn™ 2210 and Vistane™ LMMH (100 parts/167 parts respectively) were dissolved in heptane at 20% solids in a 3.8 liter glass jar using a lightning mixer for 24 hours. Each of the master batches were then rolled on a roll mixer for 24 hrs at room temperature in the 3.8 liter containers. The appropriate amounts of both master batches are then weighted into 0.9 liter glass jars to achieve the desired ratios for the adhesive blend. The jars are then allowed to mix on a roll mixer overnight at room temperature.

The blends of the acrylate/Natsyn™ 2210Vistanex™ LMMH were then coated onto a Daubert release liner to achieve a dry coating thickness of 57 microns. A knife over bed coater was used for the coating. The adhesive was dried in a dual oven system and the oven temperatures are listed below. After the adhesive was dry it was laminated to the woven cloth backing described in Example 4A.

| Sample # | Acrylate/Elastomer Tackifier | solids % | coating thickness (microns) | orifice (microns) | speed (m/min.) | zone 1 (C) | zone 2 (C) |
|---|---|---|---|---|---|---|---|
| 4F | 100/0/0 | 20 | 57 | 470 | 1.1 | 33 | 153 |
| 4G | 75/9/16 | 20 | 57 | 470 | 1.1 | 35 | 153 |
| 4H | 50/19/31 | 20 | 57 | 500 | 1.1 | 35 | 153 |
| 4I | 25/28/47 | 20 | 57 | 424 | 1.1 | 37 | 135 |
| 4J | 0/37/63 | 20 | 57 | 381 | 1.1 | 37 | 135 |

The tape samples of the various ratios of acrylate/elastomer pressure-sensitive adhesive blend were tested for skin adhesion. Durapore™ Brand adhesive tape available from 3M of St. Paul, Minn. was tested as a Competitive Sample.

| Sample # | Acrylate/Elastomer/ Tackifier Ratio | $T_0$ N/dm | $T_{48}$ N/dm | Lift | Residue |
|---|---|---|---|---|---|
| 4F | 100/0/0 | 1.8 | 7.0 | 0.6 | 0.3 |
| 4G | 75/9/16 | 1.9 | 8.0 | 0.8 | 0.5 |
| 4H | 50/19/31 | 2.4 | 7.0 | 0.7 | 0.7 |
| 4I | 25/28/47 | 1.6 | 4.4 | 1.1 | 0.4 |
| 4J | 0/37/63 | 2.6 | 2.1 | 1.5 | 0.5 |
| Control | Durapore ™ | 2.5 | 6.4 | 1.4 | 0.2 |

Both hot melt and solvent coated acrylate/elastomer blend pressure-sensitive adhesives perform satisfactorily when coated on a non-occlusive backing and adhered to skin. This is apparent when examining the initial adhesion values and the adhesion after 48 hours. The lift and residue results are also desirable for adhesives blends prepared by solvent or by hot melt blending.

EXAMPLE 5

Example 5 demonstrates that the acrylate/elastomer pressure-sensitive adhesive blends of the invention perform well when coated on the cloth/polymer composite backing as described in Example 3 above.

5A. Hot Melt Coated Acrylate/Elastomer Adhesive Blends Coated on Cloth/Polymer Composite Backing The adhesive used to prepare the samples in Example 4A above was used to coat the cloth/composite backings described in Example 3 above. The adhesive was coated at an average thickness of 50 microns.

Samples were tested for skin adhesion properties including initial adhesion, adhesion after 48 hours, lift and the amount of adhesive residue remaining after removal of the sample (residue) and results are shown in the table below.

| Sample # | Acrylate/Elastomer/ Tackifier Ratio | $T_0$ N/dm | $T_{48}$ N/dm | Lift | Residue |
|---|---|---|---|---|---|
| 5A | 100/0/0 | — | — | — | — |
| 5B | 75/9/16 | 2.3 | 9.6 | 0.5 | 0.7 |
| 5C | 50/19/31 | 2.4 | 8.6 | 0.4 | 0.5 |
| 5D | 25/28/47 | 2.0 | 3.6 | 1.0 | 0.8 |
| 5E | 0/37/63 | 1.1 | 1.6 | 0.7 | 0.8 |

Samples 5B through 5E demonstrate the $T_0$ values of the blend adhesives show a synergistic effect. The skin adhesion, $T_0$ and $T_{48}$, are determined by the ratio of the adhesive components.

5B. Solvent Coated Acrylate/Elastomer Adhesive Bends Coated on Cloth/Polymer Composite Backing The adhesives prepared in Example 4B above were coated onto the cloth/polymer composite backing as prepared in Example 3 above. Coating weight and processing conditions are listed in the table below.

| Sample # | Acrylate/ Elastomer/ Tackifier | solids % | orifice (microns) | speed (ml/min.) | zone (C) | zone 2 (C) |
|---|---|---|---|---|---|---|
| 5F | 100/0/0 | 20 | 386 | 1.1 | 37 | 135 |
| 5G | 75/9/16 | 20 | 368 | 1.1 | 37 | 135 |
| 5H | 50/19/31 | 20 | 368 | 1.1 | 37 | 135 |
| 5I | 25/28/47 | 20 | 312 | 1.1 | 37 | 135 |
| 5J | 0/37/63 | 20 | 312 | 1.1 | 37 | 135 |

Samples were tested for skin adhesion properties including initial adhesion, adhesion after 48 hours, lift and the amount of adhesive residue remaining after removal of the sample (residue) and results are shown in the table below.

| Sample # | Acrylate/Elastomer/ Tackifier Ratio | $T_0$ N/dm | $T_{48}$ N/dm | Lift | Residue |
|---|---|---|---|---|---|
| 5F | 100/0/0 | 2.0 | 9.5 | 0.2 | 0.4 |
| 5G | 75/9/16 | 2.2 | 7.5 | 0.6 | 0.5 |
| 5H | 50/19/31 | 2.0 | 6.0 | 0.7 | 0.5 |
| 5I | 25/28/47 | 1.9 | 2.8 | 0.8 | 0.4 |
| 5J | 0/37/63 | 1.5 | 1.4 | 0.7 | 0.7 |
| Control | J&J ™ | 0.7 | 2.8 | 1.9 | 2.23 |

Samples 5F–5J demonstrate that the blend of adhesives used for Samples 5G–5I offer usually higher $T_0$ than the individual components used to prepare Samples 5F–5J. The blends show a synergistic effect and not an additive effect. The skin adhesion, $T_0$ and $T_{48}$, is determined by the ratio of the components.

The competitive Sample ZONAS POROUS™ Brand Adhesive Tape from Johnson and Johnson Medical, Inc. was included to demonstrate that both hot melt and solvent coated acrylate/elastomer adhesive blends on low porosity (occlusive) backings are competitive with a commercially available tape.

EXAMPLE 6/COMPARATIVE EXAMPLE 6

For Samples 6A, 6B, and 6C, pressure-sensitive adhesive tapes were prepared with the acrylate adhesive A. A thermoplastic elastomeric adhesive (prepared by blending 50 parts thermoplastic elastomeric block copolymer KRATON™ D1107P, 1 part antioxidant IRGANO™ 1010 and 50 parts tackifying resin ESCOREZ™ 1310LC) was melt blended using a corotating twin screw extruder described in Example 4A with the thermoplastic elastomeric block copolymer fed into zone 1 of the extruder, the tackifier into zone 2 and the acrylic pressure-sensitive adhesive fed into zone 3. Temperatures were maintained between 149° C. and 165° C. The blend was extruded using a contact die with a feed rate of 6.4 Kg/hr to form a pressure-sensitive adhesive tape. The acrylic adhesive to thermoplastic elastomer adhesive ratio had ratios of 75:25, 50:50 and 25:75 for Samples 6A, 6B, and 6C respectively. For Sample 6D, a pressure-sensitive adhesive tape was prepared with acrylate Adhesive B and the thermoplastic elastomer, KRATON™ D1107P (99 parts preblended with 1 part IRGANOX 1010 antioxidant), with the acrylic pressure-sensitive adhesive to thermoplastic elastomer block copolymer ratio being 75:25. For Comparative Sample C6E, the pressure-sensitive adhesive tape was prepared using only acrylic adhesive. For Comparative Sample C6F, the pressure-sensitive adhesive tape was prepared using only the tackified thermoplastic elastomeric adhesive. All samples had an adhesive coating thickness of about 50 μm (2 mils) and were coated onto non-occlusive, i.e. breathable, woven backing which has an 180×48 plain weave acetate taffeta cloth, 75 denier fiber in the warp direction and 150 denier fiber in the weft direction, available from Milliken and Co., Spartanburg, Ga. The adhesive compositions in Samples 6A and 6D showed a substantially continuous acrylic adhesive domain with the thermoplastic elastomer/tackifying resin forming schistose ribbon-like domains. In the adhesive composition of Sample 6B, the acrylic adhesive and the thermoplastic elastomer/tackifying resin formed substantially co-continuous schistose domains. In Sample 6C, the thermoplastic elastomer/tackifying resin formed a substantially continuous domain, while the acrylic adhesive formed schistose ribbon-like domains. The pressure-sensitive adhesive tapes were tested for skin adhesion immediately after application, $T_0$, and after 24 hours, $T_{24}$, skin adhesion lift after 24 hours and skin adhesion residue after 24 hours. The results are set forth in the table below.

| Sample | $T_0$ (N/dm) | $T_{24}$ (N/dm) | $T_{24}$ Lift | $T_{24}$ Residue |
|---|---|---|---|---|
| C6E | 2.2 | 7.9 | 1.8 | 1.0 |
| 6A | 3.0 | 11.2 | 1.6 | 0.8 |
| 6B | 4.0 | 7.7 | 1.6 | 0.6 |
| 6C | 3.4 | 4.3 | 1.6 | 0.3 |
| C6F | 3.0 | 3.3 | 1.3 | 0.1 |
| 6D | 2.0 | 2.7 | 0.3 | 1.0 |

As can be seen from the data in the table above, the pressure-sensitive adhesive tapes on Samples 6A, 6B, 6C and 6D had enhanced peel performance from skin and the $T_0:T_{24}$ adhesion can be controlled by appropriate blending of the acrylic adhesive and the tackified or untackified thermoplastic elastomer. In particular, the tape of Sample 6B had between 180 percent and 33 percent higher initial adhesion to skin than tapes prepared of either of the component pressure-sensitive adhesives, Comparative Samples C6E and C6F. Additionally, all Samples provided adhesives with acceptable 24 hour aged adhesion to skin.

EXAMPLE 7

For Sample 7A, the acrylic pressure-sensitive adhesive used in Example 6 was melt-blended with a thermoplastic elastomeric adhesive (prepared by preblending 100 parts thermoplastic elastomeric block copolymer KRATON™ D1107P, 1.5 parts antioxidant IRGANOX™ 1076, available from Ciba-Geigy Corp, 1.5 parts antioxidant CYANOX™ LTDP, available from American Cyanamide of Wayne, N.J., and 70 parts tackifying resin WINGTACK™ Plus, available from Goodyear Tire and Rubber Company of Akron, Ohio) with the acrylic adhesive to thermoplastic elastomer adhesive ratio being 65:35 using the process described in Example 1A onto a non-occlusive woven backing as used in Example 6. The adhesive coating had an average thickness of approximately 50 μm (2 mils). For Sample 7B, a pressure-sensitive adhesive tape was prepared as for Sample 7A except the thermoplastic elastomeric adhesive was prepared by blending 50 parts thermoplastic elastomeric block copolymer KRATON™ D1119, a styrene-isoprene-styrene block copolymer, shear viscosity –17 Pa-s, available from Shell Chemical Co), 2 parts antioxidant IRGANOX™ 1076 and 48 parts tackifying resin WINGTACK™ Plus. For Sample 7C, a pressure-sensitive adhesive tape was prepared as for Sample 7A except the acrylic pressure-sensitive adhesive used in Example 6 was melt-blended with a thermoplastic elastomeric adhesive, prepared by blending 50 parts thermoplastic elastomeric block copolymer KRA- TON™ D1107P, 1 part antioxidant IRGANOX™ 1010, and 50 parts tackifying resin ESCOREZ™ 1310 LC, with the acrylic adhesive to thermoplastic elastomer adhesive ratio being 25:75. The adhesive compositions in Samples 7A and 7B showed a substantially continuous acrylic adhesive domains with the thermoplastic elastomer/tackifying resin forming schistose ribbon-like domains. The adhesive compositions in Sample 7C showed a substantially continuous thermoplastic elastomer/tackifying resin domain with the acrylic adhesive forming schistose ribbon-like domains. The pressure-sensitive adhesive tapes were tested for skin adhesion immediately after application, $T_0$, and after 48 hours, $T_{48}$, skin adhesion lift after 48 hours and skin adhesion residue after 48 hours. The results are set forth in the table below.

| Sample | $T_0$ (N/dm) | $T_{48}$ (N/dm) | $T_{48}$ Lift | $T_{48}$ Residue |
|---|---|---|---|---|
| 7A | 4.9 | 12.0 | 1.9 | 1.6 |
| 7B | 4.6 | 10.8 | 1.9 | 1.7 |
| 7C | 2.1 | 5.4 | 0.7 | 0.3 |

As can be seen from the data in the table above, the pressure-sensitive adhesive tapes of Samples 7A, 7B, and 7C, with non-occlusive woven backings and with different acrylic pressure-sensitive adhesives and thermoplastic elastomeric adhesives, had acceptable peel performance from skin.

EXAMPLE 8

For Samples 8A, 8B, and 8C, pressure-sensitive adhesive tapes were made with various non-occlusive backings using the same thermoplastic elastomer/tackifying resin adhesive, melt-mixing and coating process used to prepare Sample 7C above. For Sample 8A, the acrylic adhesive to thermoplastic elastomer adhesive ratio was 60:40 and the pressure-sensitive adhesive composition was coated onto a release liner and laminated to a nonwoven rayon fiber backing. The backing was as described in Example 1A. For Sample 8B, the acrylic adhesive to thermoplastic elastomer adhesive ratio was 50:50 and the pressure-sensitive adhesive composition was applied to a liner and melt blown microfiber, with a diameter of between 5 and 10 $\mu$m and made by using PS 440–200 polyurethane, available from Morton International, Seabrook, N.H., and a process similar to that describe in U.S. Pat. No. 5,230,701, Example 1, was blown onto the adhesive at 450 g/hr/cm to form a 80 $\mu$m thick backing with a basis weight of 20 g/m². For Sample 8C, the acrylic adhesive to thermoplastic elastomer adhesive ratio was 60:40 and the pressure-sensitive adhesive composition was applied to 0.65 mm thick SONTARA™ 8010 backing (a 44 g/m² basis weight hydro-entangled polyester nonwoven substrate available from DuPont). In the adhesive composition used to prepare Samples 8A, 8B, and 8C, the acrylic adhesive and the thermoplastic elastomer/tackifying resin adhesive formed substantially co-continuous schistose domains. The pressure-sensitive adhesive tapes were tested for skin adhesion immediately after application, $T_0$, and after 48 hours, $T_{48}$, skin adhesion lift after 48 hours and skin adhesion residue after 48 hours. The thickness of each of the adhesive composition and the test results are set forth in the table below.

| Sample | Thickness ($\mu$m) | $T_0$ (N/dm) | $T_{48}$ (N/dm) | $T_{48}$ Lift | $T_{48}$ Residue |
|---|---|---|---|---|---|
| 8A | 21 | 2.1 | 6.5 | 0.1 | 0.6 |
| 8B | 39 | 2.6 | 6.1 | 0.5 | 0.0 |
| 8C | 32 | 3.5 | 12.0 | 0.9 | 4.8 |

As can be seen from the data in the table above, the pressure-sensitive adhesive tapes on Samples 8A, 8B and 8C, with non-occlusive woven backings and with different acrylic pressure-sensitive adhesives and thermoplastic elastomeric adhesives, had acceptable peel performance from skin.

EXAMPLE 9

For Samples 9A, 9B, 9C, and 9D, pressure-sensitive adhesive tapes were made as in Example 8 except with various occlusive non-breathable backings. For Sample 9A, the acrylic adhesive to thermoplastic elastomer adhesive ratio was 60:40 and the pressure-sensitive adhesive composition was applied to a 117 $\mu$m thick polyethylene/vinyl acetate copolymer film prepared using ESCORENE™ S-31209, available from Exxon Chemical Co. The film was perforated with 97 holes/cm². For Sample 9B, the acrylic adhesive to thermoplastic elastomer adhesive ratio was 60:40 and the pressure-sensitive adhesive composition was applied to a 76 $\mu$m thick low density polyethylene film, prepared using NA 964-085 resin, available from Quantum Chemical Co. For Sample 9C, the acrylic adhesive to thermoplastic elastomer adhesive ratio was 50:50 and the pressure-sensitive adhesive composition was applied to 0.57 mm thick plasticized polyvinyl chloride foam (available as No. 9058 TA 022 Fleshtone from General Foam Corp., Carlstat, N.J.). For Sample 9D, the acrylic adhesive to thermoplastic elastomer adhesive ratio was 50:50 and the pressure-sensitive adhesive composition was applied to the polymer side of a white polymer/cloth composite as described in Example 3 above. In the adhesive composition of Samples 9A, 9B and 9D, the acrylic adhesive and the thermoplastic elastomer/tackifying resin adhesive formed substantially co-continuous schistose domains. In the adhesive composition used for Sample 9C, the acrylic adhesive formed a substantially continuous domain and the thermoplastic elastomer/tackifying resin adhesive formed ribbon-like schistose domains. The pressure-sensitive adhesive tapes were tested for skin adhesion immediately after application, $T_0$, and after 48 hours, $T_{48}$, skin adhesion lift after 48 hours and skin adhesion residue after 48 hours. The thickness of each of the adhesive composition examples and the test results are set forth in the table below.

| Sample | Thickness ($\mu$m) | $T_0$ (N/dm) | $T_{48}$ (N/dm) | $T_{48}$ Lift | $T_{48}$ Residue |
|---|---|---|---|---|---|
| 9A | 29 | 2.4 | 1.8 | 1.3 | 0.6 |
| 9B | 39 | 2.1 | 1.5 | 0.9 | 0.6 |
| 9C | 39 | 5.6 | 7.6 | 0.3 | 1.8 |
| 9D | 50 | 1.5 | 3.7 | 1.1 | 0.3 |

EXAMPLE 10

Samples 10A, 10B, 10C, 10D, and 10E were prepared in the following manner. For Sample 10A the adhesive was prepared using an acrylate adhesive B and elastomeric CV60 (a natural rubber, shear viscosity—2089 Pa-s as in Example 4A except process conditions were different and ESCORBZ 13101 were melt-blended. The extruder ran at 166 rpm and the temperature progressively increased from 93 °C. to 149 °C. from zone 1 to zone 4 was maintained at 149 °C. in the remaining zones and the die temperature was between 160° C. and 168° C. The feed rates were adjusted to provide a ratio of pressure-sensitive adhesive to elastomeric polymer of 33:67 where the elastomer/tackifier pressure-sensitive adhesive, shear viscosity—126 Pa-s, was in a ratio of 100 parts elastomer to 100 parts tackifier. For Sample 10B, the acrylic pressure-sensitive adhesive to elastomer/tackifier pressure-sensitive adhesive ratio was 50:50 where the elastomer/tackifier pressure-sensitive adhesive, shear viscosity—74 Pa-s, was in a ratio of 100 parts elastomer to 200 parts tackifier. For Sample 10C, elastomeric NAT-SYN™ 2210 was added in barrel 2 and a tackifying resin, WINGTACK™ 95 (available from Goodyear Tire and Rubber Co.) was added in barrel 1, were melt blended with the acrylic pressure-sensitive adhesive to provide acrylic pressure-sensitive adhesive to elastomer/tackifier pressure-sensitive adhesive in a ratio of 50:29:21, where the elastomer/tackifier pressure-sensitive adhesive, shear viscosity—174 Pa-s, was in a ratio of 100 parts elastomer to 70 parts tackifier. Process conditions were as 4A except zone 1 was 163° C., zone 2 was 174° C., zone 4 was 175° C., zone 5 was 176° C., zone 6 was 174° C., die temperature was 177° C. Coating speed was 5.8m/min. For Sample 10D, the elastomer/tackifier pressure-sensitive adhesive, shear viscosity—562 Pa-s, of the pressure-sensitive adhesive composition was composed of 100 parts elastomeric VISTANEX™ MM L-80 (polyisobutylene; MW 990,000) in barrel 2, 48 parts VISTANEX™ LM-MH in barrel 1, and 32 parts of WINGTACK™ 95, in barrel 4, and the acrylic pressure-sensitive adhesive to elastomer/tackifier pressure-sensitive adhesive was in a ratio of 50:50. Process conditions were as 10C except zone 1 was 149° C., zone 2 was 175° C., zone 3 was 204° C., zone 5 was 198° C., zone 6 was 207° C., die temperature was 204° C. For Sample 10E, the elastomeric polymer, shear viscosity —258 Pa-s, of the pressure-sensitive adhesive composition was composed of 100 parts elastomeric AMERIPOL™ 1011 A (styrene butadiene rubber) added in barrel 2, and 100 parts tackifier FORAL™ 85 (available from Hercules, Inc.), added in barrel 1, and the acrylic pressure-sensitive adhesive to elastomer/tackifier pressure-sensitive adhesive was in a ratio of 50:50. Process conditions were as 10C except zone 1 was 83° C., zone 2 was 89° C., zone 3 was 94° C., zone 4 was 94° C., zone 5 was 94° C., zone 6 was 94° C., die temperature was 106° C.

The pressure-sensitive adhesives of Samples 10A and 10B were coated onto a non-occlusive, i.e. breathable, woven backing consisting of 62×56 cotton cloth from Burcott Mills, Chicago, Ill. The pressure-sensitive adhesives of Samples 10C, 10D and 10E were coated onto a non-occlusive, i. e. breathable, woven backing described in Example 4. The thickness of the pressure-sensitive adhesive coating was 52 $\mu$m, 43 $\mu$m, 57 $\mu$m, 57 $\mu$m and 57 $\mu$m, respectively. The pressure-sensitive adhesive tapes were tested for skin adhesion immediately after application, $T_0$, and after 48 hours, $T_{48}$, skin adhesion lift after 48 hours and skin adhesion residue after 48 hours. The results are set forth in the table below.

| Sample | $T_0$ (N/dm) | $T_{48}$ (N/dm) | $T_{48}$ Lift | $T_{48}$ Residue |
|---|---|---|---|---|
| 10A | 1.5 | 3.3 | 1.3 | 0.3 |
| 10B | 1.9 | 6.9 | 0.3 | 0.5 |
| 10C | 3.2 | 9.9 | 0.7 | 0.9 |
| 10D | 2.3 | 3.9 | 0.9 | 0.6 |
| 10E | 4.8 | 8.9 | 0.6 | 0.8 |

As can be seen from the data in the table below, the pressure-sensitive adhesive tapes on Samples 10A, 10B, 10C, 10D, and 10E, with non-occlusive woven backings and with different acrylic pressure-sensitive adhesives and elastomeric adhesives, had acceptable peel performance from skin.

EXAMPLE 11

For Samples 11 A, 11B, and 11C, pressure-sensitive adhesive tapes were made in the following manner. The pressure-sensitive adhesives were prepared according to the method outlined in Example 4C. The pressure-sensitive adhesive was applied to a non-occlusive, i.e., breathable, backing or one of two occlusive, i.e., nonbreathable, backings. For Sample 11A, the pressure-sensitive adhesive composition was coated onto a release liner and laminated to a nonwoven backing described in Example 1A. For Sample 11B, the pressure-sensitive adhesive composition was applied to a 117 $\mu$m thick polyethylene/vinyl acetate copolymer film (made with ESCORENE™ LD-312.09 resin available from Quantum Chemical Co. of Cincinnati, Ohio) which had been previously perforated with 97 holes/cm². For Sample 11C, the pressure-sensitive adhesive composition was applied to the polymer side of the polymer/cloth composite described in Example 3. In the adhesive composition of Samples 11A, 11 B, and 11C, the acrylic adhesive and the elastomeric pressure-sensitive adhesive formed substantially co-continuous schistose domains. The pressure-sensitive adhesive tapes were tested for skin adhesion immediately after application, $T_0$, and after 48 hours, $T_{48}$, skin adhesion lift after 48 hours and skin adhesion residue after 48 hours. The thickness of each of the adhesive composition examples and the test results are set forth in the table below.

| Example | Thickness ($\mu$m) | $T_0$ (N/dm) | $T_{48}$ (N/dm) | $T_{48}$ Lift | $T_{48}$ Residue |
|---|---|---|---|---|---|
| 11A | 21 | 2.6 | 7.9 | 0.5 | 0.9 |
| 11B | 29 | 3.5 | 2.9 | 1.3 | 1.1 |
| 11C | 50 | 3.9 | 5.1 | 1.0 | 1.4 |

As can be seen from the data in the table above, the pressure-sensitive adhesive tapes of Sample 11A, on non-occlusive breathable backings, and of Samples 11B and 11C, on occlusive nonbreathable backings had acceptable but varying peel performance from skin.

We claim:

1. A pressure-sensitive adhesive composition suitable for medical applications comprising a blend of at least two components comprised of about 5 to 95 weight percent of a first component comprised of an acrylic pressure-sensitive adhesive and about 5 to 95 weight percent of a second component comprised of either (a) a thermoplastic elastomer, or (b) an elastomer with a tackifying resin, said composition having an anisotropic morphology comprising two axes perpendicular to each other, both parallel to a major surface said axes comprising a longitudinal axis in the film-forming direction and a transverse axis in the cross-web direction, said morphology further comprising at least two distinct domains, a first domain being substantially continuous in nature and a second domain being fibrillose to schistose in nature and oriented along the film-forming direction and parallel to a major surface of the adhesive composition within said first domain, wherein the resulting pressure-sensitive adhesive demonstrates a $T_0$ of at least 1 Newton per decimeter and a $T_{48}$ of less than 12 Newtons per decimeter when adhered to skin according to the Skin Adhesion Test as defined herein.

2. The pressure-sensitive adhesive composition of claim 1 wherein the acrylic pressure-sensitive adhesive comprises a polymer of a $C_3$–$C_{12}$ alkyl ester.

3. The pressure-sensitive adhesive composition of claim 1 wherein the acrylic pressure-sensitive adhesive comprises a polymer of isooctyl acryl ate, 2-ethyl-hexyl acrylate or n-butyl acrylate.

4. The pressure-sensitive adhesive composition of claim 1 wherein the acrylic pressure-sensitive further comprises a polar component.

5. The pressure-sensitive adhesive composition of claim 1 wherein the polar component is selected from the group consisting of acrylic acid, methacrylic acid, ethylene vinyl acetate, N-vinyl pyrrolidone and styrene macromer.

6. The pressure-sensitive adhesive composition of claim 5 wherein the acrylic pressure-sensitive adhesive comprises about 100 to 80 weight percent alkyl ester component and about 0 to 20 weight percent polar component.

7. The pressure-sensitive adhesive composition of claim 1 wherein the thermoplastic elastomeric materials comprise linear, radial, star, tapered or branched copolymers.

8. The pressure-sensitive adhesive composition of claim 7 wherein the thermoplastic elastomeric materials are selected from the group consisting of styrene-isoprene block copolymers, styrene-(ethylene-butylene) copolymers, styrene-(ethylene-propylene) block copolymers, styrene-butadiene block copolymers, polyetheresters and poly-alpha-olefins.

9. The pressure-sensitive adhesive composition of claim 1 further comprising a tackifying resin.

10. The pressure-sensitive adhesive composition of claim 9 wherein said tackifying resin comprises up to 200 weight percent based on the weight of either (a) the elastomeric material or (b) the thermoplastic elastomeric material.

11. The pressure-sensitive adhesive composition of claim 1 wherein the elastomeric materials are selected from the group consisting of natural rubber, butyl rubber, ethylene-propylene, polybutadiene, synthetic polyisoprene, and styrene-butadiene random copolymers.

12. A method for preparing a medical pressure-sensitive adhesive layer comprising the steps of (1) blending at least two components comprised of about 5 to about 95% by weight of a first component comprised of at least one acrylic pressure-sensitive adhesive and about 5 to about 95% by weight of a second component comprised of either (a) at least one elastomer with a tackifying resin, or (b) at least one thermoplastic elastomer, wherein the resulting pressure-sensitive adhesive, and (2) coating said adhesive to form a layer, wherein said adhesive demonstrates a $T_0$ of at least 1 N/dm and a $T_{48}$ of less than 12 N/dm when adhered to skin according to the Skin Adhesion Test as defined herein.

13. The method of claim 12 wherein said blending step is comprised of melt blending said materials under shear or extensional conditions or both and wherein said coating step is comprised of forming and drawing said melt blend to form a pressure-sensitive adhesive composition having an anisotropic morphology comprising two axes perpendicular to each other both parallel to a major surface, said axes comprising a longitudinal axis in the film-forming direction and a transverse axis in the cross-web direction, said morphology further comprising at least two distinct domains, a first domain being substantially continuous in nature and a second domain being fibrillose to schistose in nature and oriented along the film-forming direction and parallel to a major surface of the adhesive composition within said first domain.

14. The method of claim 13 further comprising the step of allowing said composition to cool.

15. The method of claim 13 wherein the melt blending is carried out under dispersive or distributive conditions or a combination thereof.

16. The method of claim 13 wherein the blending is carried out using either a batch or continuous process.

17. The method of claim 16 wherein the batch process is carried out using internal mixing or roll milling.

18. The method of claim 16 wherein the continuous process is carried out using a single screw extruder, a twin screw extruder, a disk extruder, a reciprocating single screw extruder or a pin barrel single screw extruder.

19. The method of claim 12 wherein said blending step is comprised of solvent blending and said coating step is comprised of knife coating, rollcoating, gravure coating, rod coating, curtain coating, and air knife coating.

20. The method of claim 19 further comprising the step of drying said adhesive layer.

21. A method for preparing a medical pressure-sensitive adhesive comprising solvent blending at least two components comprised of about 5 to about 95% by weight of a first component comprised of at least one acrylic pressure-sensitive adhesive and about 5 to about 95% by weight of a second component comprised of either (a) at least one elastomer with a tackifying resin, or (b) at least one thermoplastic elastomer, wherein the resulting pressure-sensitive adhesive demonstrates a $T_0$ of at least 1 N/dm and a $T_{48}$ of less than 12 N/dm when adhered to skin.

22. A pressure-sensitive medical adhesive article comprising a backing, a pressure-sensitive adhesive composition comprising a blend of about 5 to 95 weight percent of an acrylic pressure-sensitive adhesive and about 5 to 95 weight percent of a thermoplastic elastomeric block copolymer, said composition having an anisotropic morphology comprising two axes perpendicular to each other, both parallel to a major surface, said axes comprising a longitudinal axis in the film-forming direction and a transverse axis in the cross-web direction said morphology further comprising at least two distinct domains, a first domain being substantially continuous in nature and a second domain being fibrillose to schistose in nature and oriented along the film-forming direction and parallel to a major surface of the adhesive composition within said first domain, wherein the resulting pressure-sensitive adhesive demonstrates a $T_0$ of at least 1 N/dm and a $T_{48}$ of less than 12 N/dm when adhered to skin.

23. The pressure-sensitive medical adhesive article of claim 22 wherein the backing is selected from the group consisting of a woven substrate, a nonwoven substrate, a film, a foam, a melt blown web or laminates thereof.

* * * * *

UNITED STATES PATENT AND TRADEMARK OFFICE
CERTIFICATE OF CORRECTION

PATENT NO. : 5,876,855

DATED : March 2, 1999

INVENTOR(S) : Roy Wong, Dennis L. Krueger, Patrick D. Hyde, Felix P. Lau, Eumi Pyun, Pamela S. Tucker Page 1 of 3

It is certified that error appears in the above-identified patent and that said Letters Patent is hereby corrected as shown below:

On the Title page, item [56]:
In the References Cited U.S. Patent Documents, please add the following:

| | | |
|---|---|---|
| Re. 24, 906 | 12/60 | Uhlrich |
| 3,246,049 | 04/66 | Webber |
| 3,437,622 | 04-69 | Dahl |
| 3,890,407 | 06/75 | Briggs, Jr., et al. |
| 3,975,463 | 08/76 | Hirata et al. |
| 4,082,705 | 04/78 | Beede et al. |
| 4,107,233 | 08/78 | Hansen |
| 4,243,500 | 06/81 | Glennon |
| 4,288,358 | 09/81 | Trotter et al. |
| 4,410,482 | 10/83 | Subramanian |
| 4,438,232 | 03/84 | Lee |
| 4,444,817 | 04/84 | Subramanian |
| 4,554,324 | 11/85 | Husman et al. |
| 4,619,979 | 10/86 | Kotnour et al. |
| 4,699,842 | 10/87 | Jorgensen et al. |
| 4,732,808 | 03/88 | Krampe et al. |
| 4,810,523 | 03/89 | Williams et al. |
| 4,833,179 | 05/89 | Young et al. |
| 4,835,217 | 05/89 | Jorgensen et al. |
| 4,912,169 | 03/90 | Whitmire et al. |
| 4,952,650 | 08/90 | Young et al. |
| 4,994,267 | 02/91 | Sablotsky |
| 5,143,972 | 09/92 | Groves |

UNITED STATES PATENT AND TRADEMARK OFFICE
CERTIFICATE OF CORRECTION

PATENT NO.: 5,876,855                                    Page 2 of 3

DATED: March 2, 1999

INVENTOR(S): Roy Wong, Dennis L. Krueger, Patrick D. Hyde, Felix P. Lau, Eumi Pyun, Pamela S. Tucker It is certified that error appears in the above-identified patent and that said Letters Patent is hereby corrected as shown below

| | | |
|---|---|---|
| 5,198,064 | 03/93 | Tani et al. |
| 5,202,361 | 04/93 | Zimmerman et al. |
| 5,206,288 | 04/93 | Gosiewski et al. |
| 5,209,971 | 05/93 | Babu et al. |
| 5,229,206 | 07/93 | Groves |
| 5,230,701 | 07/93 | Meyer et al. |
| 5,257,491 | 11/93 | Rouyer et al. |
| 5,266,399 | 11/93 | Babu et al. |
| 5,284,889 | 02/94 | Pyun et al. |
| 5,286,781 | 02/94 | Gotoh et al. |
| 5,290,842 | 03/94 | Sasaki et al. |
| 5,296,561 | 03/94 | Babu et al. |
| 5,300,291 | 08/94 | Sablotsky et al. |
| 5,382,451 | 01/95 | Johnson et al. |
| 5,385,783 | 01/95 | Patel et al. |

In the References Cited Foreign Patent Documents, please add the following:
| | | |
|---|---|---|
| WO 93/07228 | 15.04.93 | PCT |
| WO 93/20165 | 14.10.93 | PCT |
| WO 93/23224 | 25.11.93 | PCT |
| WO 94/24221 | 27.10.94 | PCT |

UNITED STATES PATENT AND TRADEMARK OFFICE
CERTIFICATE OF CORRECTION

PATENT NO.: 5,876,855

DATED: March 2, 1999

INVENTOR(S): Roy Wong, Dennis L. Krueger, Patrick D. Hyde, Felix P. Lau, Eumi Pyun, Pamela S. Tucker It is certified that error appears in the above-identified patent and that said Letters Patent is hereby corrected as shown below

| | | |
|---|---|---|
| 0 312 228 | 19.04.89 | Europe |
| 0 352 901 | 31.01.90 | Europe |
| 0 457 566 | 21.11.91 | Europe |
| SHO 60-226579 | 11.11.95 | Japan |
| HEI 4-18344 | 22.01.92 | Japan |
| HEI 5-98223 | 20.04.93 | Japan |
| 2-2206671 claims | 16.08.90 | Japan |
| JP07003235 abstract | | Japan |
| 2 241 829 | 07.03.74 | Germany |

Signed and Sealed this

Eleventh Day of July, 2000

Attest:

Attesting Officer

Q. TODD DICKINSON

Director of Patents and Trademarks